US006030616A

United States Patent [19]
Waters et al.

[11] Patent Number: 6,030,616
[45] Date of Patent: Feb. 29, 2000

[54] HEPATITIS B ESCAPE MUTANT SPECIFIC BINDING MOLECULES

[75] Inventors: Jennifer Anne Waters, Hertfordshire; William Frederick Carman, Glasgow; Howard Christopher Thomas, London, all of United Kingdom

[73] Assignee: Imperial College of Science, Technology & Medicine, London, United Kingdom

[21] Appl. No.: 08/519,981

[22] Filed: Aug. 28, 1995

[30] Foreign Application Priority Data

Mar. 24, 1993 [GB] United Kingdom .................... 9306087
Jun. 4, 1993 [GB] United Kingdom .................... 9311526
Mar. 24, 1994 [WO] WIPO ...................... PCT/GB94/00609

[51] Int. Cl.[7] ........................... C12N 5/12; A61K 39/395; C12Q 1/70
[52] U.S. Cl. .................................... 424/149.1; 424/130.1; 424/161.1; 530/387; 530/388.3; 435/5; 435/7.1; 435/69.1; 435/70.21; 435/339; 435/346; 435/975
[58] Field of Search ................................ 435/5, 7.1, 69.1, 435/70.21, 339, 346, 975; 424/130.1, 149.1, 161.1; 530/387, 388.3

[56] References Cited

FOREIGN PATENT DOCUMENTS 0 511 855 A1 of 1992 European Pat. Off. .
PCT/GB91/00444 of 1991 United Kingdom .

OTHER PUBLICATIONS

The Lancet, vol. 336, Aug. 11, 1990, pp. 325–329, Carman et al 'Vaccine–induced escape mutant of hepatitis B virus'.
Journal of Medical Virology, vol. 29, 1989, pp. 196–203, Ashton–Rickardt et al, 'Mutants of HBsAg that define same antigenically essential residues in the imnmun odominant "a" region'.
Waters et al. 1991 Virus Research vol. 22 p 1–2, Jan. 1, 1991.
Lerner et al. 1981 PNAS USA 78 (6) 3403–3407, Jun. 1, 1981.
Wands et al 1984 PNAS USA 81 2237–2241, Apr. 1, 1984.

*Primary Examiner*—Donna C. Wortman
*Assistant Examiner*—Mary K Zeman
*Attorney, Agent, or Firm*—Nixon & Vanderhye P.C.

[57] ABSTRACT

Molecules which are capable of specifically binding to a hepatitis B escape mutant antigenic determinant include monoclonal antibodies secreted by the cell line SMH HBs 145/G/R/I (ECACC 92122312). SMH HBs 145/R/I (ECACC 93052626). SMH HBs 145/G/II (ECACC 93033109) or SMH HBs 145/R/II (ECACC 93033110) and other specific binding molecules cross-competitive with them. Antibodies secreted by the cell lines SM HBs 145/G/R/I and SMH HBs 145/G/R/II bind variant (escape mutant) HBsAG and wild type HBsAG. Antibodies secreted by the cell lines SMH HBs 145/R/I and SMH HBs 145/R/II bind variant but not wild type.

8 Claims, No Drawings

HEPATITIS B ESCAPE MUTANT SPECIFIC BINDING MOLECULES

This invention relates to antibodies and other binding molecules specific for certain hepatitis B viral antigens. It also relates to the use of such molecules in diagnosis and therapy.

Infection with hepatitis B virus (HBV) is a serious problem in many parts of the world, but some vaccines are now available. The commercially available vaccines against HBV generally comprise hepatitis B virus surface antigen (HEsAG) either in native or recombinant form. The Smith-Kline Beecham product ENGERIX-B™ is an example of the latter. Antigenic sub-types of HBV are defined serologically and have been shown to be due to single base changes in the region of the genome encoding HBsAG. However, until recently, all known antigenic sub-types contained the a-determinant, consisting of amino acids 124 to 147 of HBsAg. Antibody to the a-determinant conferred protection against all previously known sub-types. Recently, a vaccine-induced escape mutant of hepatitis B virus was reported (Carman et al, *The Lancet* 336 325–329 (1990)). The escape mutant was shown to have an HBsAG variant protein containing a glycine to arginine substitution mutation at position 145, which is within the a-determinant region. WO-A-9114703 relates to a vaccine based on the variant HBsAg and also discloses an antibody preparation comprising anti-variant HBsAg antibodies.

WO-A-9114703 does not, however, give any teaching on how co obtain the specificity needed to bind to the variant a-determinant region alone or which bind both to the wild type and valiant a-determinant regions. It is to these twin problems that the present invention is addressed.

According to a first aspect of the present invention, there is provided a molecule which is capable of specifically binding to a hepatitis B antigen determinant and which either is or cross-competes with a monoclonal antibody secreted by cell line SMH HBs 145/G/R/I (ECACC 92122312), SMH HBs 145/R/I (ECACC 93052626), SMH HBs 145/G/R/II (ECACC 93033109) or SMH HBs 145/R/II (ECACC 93033110).

A specific binding molecule such as an antibody cross-competes with another if it binds to precisely the same, or a conformationally linked, location as the other. Conformationally linked locations may be adjacent locations on the polypeptide chain of the antigen or they may be linked by virtue of the secondary structure of the polypeptide chain, which can cause adjacent folding of otherwise non-adjacent regions. Cross-competition experiments are relatively easy to carry out (Waters et al, *Virus Research* 22 1–12 (1991)) and so it is a straightforward matter to determine whether a given antibody or other specific binding molecule cross-competes with the monoclonal antibody specifically referred to above.

Specific binding molecules which at least partially cross-compete with the specified monoclonal antibodies (ie whose cross-competition is significantly greater than 0%) are useful in the invention. Specific binding molecules which totally cross-compete (ie whose cross-competition is not significantly less than 100%) are preferred, at least in some circumstances.

Specific binding molecules useful in the invention will often themselves be antibodies. While polyclonal antibodies are not excluded, monoclonal antibodies will generally be preferred because of their much more precise specificity. Monoclonal antibody technology has become well established since the original work by Köhler and Milstein (*Nature* 256 495 (1975)) and there are today many available protocols for the routine generation of monoclonal antibodies. Suitable techniques, for example, are those of Gefter et al, (*Somatic Cell Genetics* 3 231 (1977)), Köhler et al, (*Euro. J. Immuvirol.* 292–295 (1976)) and Goding ("Monoclonal Antibodies: Principle and Practice" (2nd Edition, 1986) Academic Press, New York). Typically, the protocol used is as follows:

(a) an experimental animal (such as a mouse) is immunologically challenged with the antigen against which antibodies are to be raised (in this case HbsAg with a Gly to Arg substitution mutation at position 145);

(b) the spleen cells of the animal are then fused to cells of a myeloma cell line, and the resultant hybridoma fusion cells plated out on selective medium;

(c) screening for specific antibodies is undertaken by any suitable technique, for example by the use of anti-immunoglobulin antibodies from another species.

While the use of human monoclonal antibodies may in principle be preferred for certain applications, particularly human therapy and in vivo diagnosis, technical difficulties render conventional hybridoma technology inappropriate for the generation of many human monoclonal antibodies. Non-human monoclonal antibodies, such as of murine origin, are therefore often used in practice.

Chimeric antibodies, particularly chimeric monoclonal antibodies, are also included within the scope of the invention. Such chimeric antibodies include sufficient amino acid sequences from SMH HBs 145/G/R/I, SMH HBs 145/R/I, SMH HBs 145/G/R/II or SMH HBs 145/R/II to have their characteristic specificity. At the minimum, the complementarity determining regions of the specified antibody will be present to a sufficient degree to maintain specificity. It may be that entire $V_H$ and $V_L$ domains will be present, or even entire antibody binding fragments such as the enzymatically derived Fab or F(ab')$_2$ fragments.

Various different technologies exist for preparing chimeric antibodies. For example, chimeric antibodies consisting of a human C region fused to a rodent V region have been described (Morrison et al, *PNAS* 81 6851–6855 (1984), Boulianne et al, *Nature* 312 643–646 (1984) and Neuberger et al, *Nature* 314 268–270 (1985)). Alternative chimeric antibody technology is the subject of WO-A-9004413 and WO-A-9116354, which relate to antibody conjugates having two or more covalently linked Fc regions.

Fully humanised antibodies, particularly monoclonal antibodies, are also within the scope of the invention. There are currently three separate methods for humanising non-human (particularly murine) antibodies. Reichmann et al, (*Nature* 332 323–327 (1988)) used site-directed mutagenesis on ssDNA. In another approach both Jones et al (*Nature* 321 522–525 (1986)) and Queen et al (*PNAS* 86 10029–10033 (1989)) constructed the whole V region using overlapping oligonucleotides incorporating the rodent complementarity-determining regions (CDRs) on a human framework. More recently, Lewis and Crowe (*Gene* 101 297–302 (1991)) have adapted polymerase chain reaction (PCR) methodology to graft rodent CDRs onto human immunoglobulin frameworks. WO-A-9316192 relates to humanised antibodies against hepatitis generally, and the teaching of this document may be applied to produce humanised antibodies in accordance with the present invention.

The amino acid sequences of the heavy and light chain variable domains of the monoclonal antibodies can be determined from cloned complementary DNA and the hypervariable regions (or complementarity determining regions—CDRs) identified according to Kabat et al (in "Sequences of Proteins of Immunological Interest", U.S. Department of Health and Human Services, U.S. Government Printing Office, 1987). Using any of the above methods these CDRs can be grafted into a human framework.

The single domain antibodies (dabs) of Ward et al (*Nature* 341 544–546 (1989)), represents another class of specific minding molecules (whether or not they are properly to be regarded as "antibodies"), which can be used in the scope of the present invention. In this approach, PCR or other appropriate technology is used to clone a $V_H$ or $V_L$ gene and express it in a heterologous host, such as E. coli.

The heavy and light chain variable domains can be amplified from the hybridoma using the polymerase chain reaction (PCR) and cloned in expression vectors. The isolated variable domains can be screened for binding to antigen and their affinity determined. Other single domain antibodies can be obtained directly by amplifying by the rearranged variable domain genes from the spleen DNA of an immunised mouse. The amplified DNA can be cloned into a vector and then screened for antigen binding activity. A refinement using bacteriophage as an expression vector allows the phage carrying the variable genes to be selected directly with antigen because they are expressed on the cell surface (McCafferty et al, *Nature* 348 552–554 (1990)).

The dAbs technology indicates how recombinant DNA methodology is completely changing the generation of molecules having specific binding capabilities. For this reason if no other, the invention should not be regarded as being restricted to antibodies, as understood in the classical sense (whether polyclonal or monoclonal). For reviews of engineered and artificial antibodies, which are generally applicable to the present invention, see Winter and Milstein, *Nature* 349 293–299 (1991) and Marks et al., *J. Bio. Chem.* 267 16007–16010 (1992), as well as the presentation by Dr Grea Winter at the Medical Research Council's conference on Successful Exploitation of Biomedical Research held in London on Mar. 7–8, 1994 (as published in the proceedings of that conference).

Specific binding molecules within the scope of the invention fall broadly into two classes, as far as their variant HBsAg binding capabilities are concerned. First, there are those molecules which only bind variant HBsAg, and not wild type HBsAg. Monoclonal antibodies secreted by the cell lines SMH HBs 145 R/I and SMH HBs 145R/II fall into this category, as do specific binding molecules which cross-compete with them. Secondly, there are those specific binding molecules which bind both variant HBsAg and wild type HBsAg. These specific binding molecules may in some instances be preferred. Examples include the monoclonal antibody secreted by SMH HBs 145/G/R/I and SMH HBs 145/G/R/II and specific binding molecules capable of cross-competing with them.

According to a second aspect of the present invention, there is provided a cell line or cell culture capable of expressing, and preferably secreting, specific binding molecules as described above.

Within this aspect of the invention are the hybridoma cell lines which have been specifically referred to above. These cell lines have been deposited at the European Collection of Animal Cell Cultures (ECACC) (PHLS Centre for Applied Microbiology and Research, Division of Biologics, Porton Down, Salisbury, Wiltshire SP4 OJG, UK) under the accession numbers and dates shown in the following table:

| Cell line | Deposit date | Accession No. |
|---|---|---|
| SMH HBs 145/G/R/I | December 23, 1992 | 92122312 |
| SMH HBs 145/G/R/II | March 31, 1993 | 93033109 |
| SMH HBs 145/R/I | May 26, 1993 | 93052626 |
| SMH HBs 145/R/II | March 31, 1993 | 93033110 |

These deposits have been made under the terms of the Budapest Treaty.

A generalised method for making other monoclonal antibodies has been described above. To ensure that they are within the scope of the invention, a simple cross competition experiment can be reacted with antibodies secreted by the deposited cell line. Other specific binding molecules within the scope of the invention can be made in accordance with the teaching of the papers and/or patent publications referred to earlier.

Specific binding molecules in accordance with the invention are useful both in diagnosis and in therapy.

In its diagnostic applications, the invention can in one embodiment be used for the differential diagnosis of variant hepatitis B as opposed to conventional hepatitis B. In this case, a specific binding molecule which either is, or has the specificity of, SMH HBs 145/R/I or SMH HBs 145/R/II can be used, as such specific binding molecules bind only to the variant. Specific binding molecules of the invention may be used for this purpose in conjunction with antibodies or other specific binding molecules which bind only to wild type hepatitis B antigens and not to those of the wild type; a suitable monoclonal antibody is RF HBs 1, which is disclosed in EP-A-0038642.

In another embodiment, the invention can be used to detect, in a single step, the presence of either wild type or variant hepatitis B. In this case, a specific binding molecule which either is, or has the specificity of, SMH HBs 145/G/R/I or SMH HBs 145/G/R/II can be used, as such specific binding molecules bind both to the wild type and the variant.

Methods of diagnosis in accordance with the invention can be carried out in vitro. According to a third aspect of the present invention, there is provided a method for the diagnosis of hepatitis B, the method comprising contacting a sample suspected No contain hepatitis B particles or antigens with a specific binding molecule as described above.

In vitro assays may take many formats. Some depend upon the use of labelled specific binding molecules such as antibodies (whose use is included within the scope of the invention), whereas some detect the interaction of antibody (or other specific binding molecule) and antigen by observing the resulting precipitation. Examples of qualitative and quantitative in vitro assays which do not rely on labelled antibodies include gel precipitation (including the double diffusion method of Ouchterlony), single radial immunodiffusion (SRID), immunoelectrophoresis, including rocket electrophoresis and two-dimensional immunoelectrophoresis, and quantification by the scattering of an incident light source (nechelometry).

More often in practice, some form of labelling is used to detect the antigen-antibody interaction. Labels may be radioactive or non-radioactive. Depending upon the format of the assay, either the specific binding molecules within the scope of the invention can be labelled, or other specific binding molecules, which bind to them are labelled. Immunoassays (including radio-immunoassays) and immunometric assays (including immunometric radioassays and enzyme-linked immunosorbent assays) can be used, as can immunoblotting techniques. Chemiluminescent and fluorescent labels are also contemplated.

In vitro assays will often be conducted using kits. According to a fourth aspect of the present invention, there is provided an assay kit for the detection of a hepatitis B particle or antigen, the kit comprising a specific binding molecule as described above and means for detecting whether the specific binding molecule is bound to a hepatitis B particle or antigen.

The assay methodology may for example be any of the assays referred to above. Competitive and, especially, sandwich immunoassay kits are preferred. The specific binding molecule and the detection means may be provided in separate compartments in the kit. The specific binding molecule may be provided bound to a solid support. The detection means will for practical preference comprise a detectably labelled second specific binding molecule (which itself may be an antibody), which binds to the antibody or other specific binding molecule referred to above.

The invention also has application in in vivo diagnosis. According to a fifth aspect of the invention, there is provided the use of a (generally labelled) specific binding molecule as described above in the preparation of an agent for the in vivo diagnosis of hepatitis B. The invention is therefore related to a method for the in vivo diagnosis of hepatitis B comprising administering to a subject, generally by parenteral means, an optionally labelled specific binding molecule as described. Labels for in vivo use include radioactive labels and paramagnetic labels, both of which can be detected by suitable external equipment.

As well as application in diagnosis, the invention can be used in therapy, particularly in the treatment of, or passive immunisation against, hepatitis B infection.

According to a sixth aspect of the invention, there is therefore provided the use of a specific binding molecule as described above in the preparation of a therapeutic or prophylactic agent against hepatitis B infection. The invention can therefore be used in a method of treating or preventing hepatitis B infection, the method comprising administering to a subject, generally parenterally, specific binding molecules as described above.

According to a seventh aspect of the invention, there is provided a formulation comprising a specific binding molecule as described above and a pharmaceutically acceptable carrier therefor.

Formulations administered parenterally to humans will generally be sterile. A carrier will be present, such as water for injections or phosphate buffered saline. The dosages and timing of the doses will be under the guidance of the clinician or physician, and will depend not only on the specificity and avidity of the specific binding molecules being administered but also on their antigenicity or other adverse features. As a general guideline, however, it is expected that a typical prophylactic regime might involve administration of from 1 to 10 mg (for example about 5 mg) weekly, and a typical treatment regime might involve from 0.5 to 5 mg (for example about 1 mg) daily for about a week and then from 0.5 to 5 mg (for example about 1 mg) weekly.

Preferred features of each aspect of the invention are as for each other aspect mutatis mutandis.

The invention will now be described by the following examples.

EXAMPLE 1
Preparation of Hybridomas Antigen

Yeast strain DC5 cir° was transformed with DNA of plasmid pRIT13557 to establish strain Y1648, as described in Example 2 or WO-A-9114703. Strain Y1648 expresses variant HBsAg, with a Gly→Arg mutation at position 145. Variant HBsAg was isolated from a culture (designated C1334) of strain Y1648 by AEROSIL™ adsorption/desorption, ultrafiltration, ion-exchange column chromatography, CsCl density gradient centrifugation and dialysis of the CsCl gradient fractions. The batch of purified antigen was designated 31M5.

Immunisation

An inbred Balb/c mouse (Harlan Olac Ltd, Bicester, Oxon, UK) was immunised with 40$\mu$g recombinant variant HBsAg from batch 31M5 emulsified with 100 $\mu$l complete Freund's adjuvant, given subcutaneously. A second dose of 20$\mu$g 31M5 emulsified with 100 $\mu$l incomplete Freund's adjuvant was given subcutaneously after four weeks. Two weeks later the mouse was given 10 $\mu$g 31M5 intravenously. The mouse was sacrificed for fusion four days later.

Fusion

The spleen cells were separately, washed and counted. They were fused with the mouse myeloma cell line P3-NS-1/1-Ag4-1 (Flow Laboratories Limited, Irvine, Scotland) at a 10:1 ratio. The fusogen was polyethyleneglycol 1500. Fusion was allowed to continue at 37° C. for seven minutes. The fused cells were plated out at $2\times10^6/2$ ml well, and the hybridomas selected using HAT medium.

EXAMPLE 2
Screening for Specific Antibodies

Supernatant from the hybridoma-containing wells obtained in Example 1 was incubated with polystyrene beads coated with either recombinant wild type ay sub-type HBsAG or 31M5 (the variant HBsAg). Antibody bound to the beads was detected with horseradish peroxidase-labelled rabbit anti-mouse immunoglobulin (Sigma Chemical Company Limited).

EXAMPLE 3
Cloning and Deposit

Selected wells were cloned by limiting dilution three times or until all wells tested were positive for the specific antibody and the line was monoclonal. Two cell lines secreting monoclonal antibody having specificity for both the variant and wild type HBsAgs were deposited at the European Collection of Animal Cell Cultures (Porton Down, Salisbury, Wiltshire) on the dates and with the accession numbers shown in the following table:

| Cell line | Deposit date | Accession No. |
| --- | --- | --- |
| SMH HBs 145/G/R/I | Dec. 23, 1992 | 92122312 |
| SMH HBs 145/G/R/II | Mar. 31, 1993 | 93033109 |

Binding of SMH HBs 145/G/R/I to mutant and wild type antigens was measured by an enzyme-linked immunosorbent assay (ELISA), as-follows. The solid phase was coated with either the mutant antigen or the wild type antigen and incubated for 16 hours at room temperature. The solid phase was then washed and then incubated with a $\frac{1}{1000}$ dilution of horseradish peroxidase-labelled rabbit anti-mouse antibody (Dako) for 2½ hours at 37° C. The solid phase was again washed and enzyme substrate added to the solid phase in a clean tube for 30 minutes. The OD reading of this liquid was measured in a multi-well plate reader at 495 nm. This was compared with an assay with a medium-only control and an irrelevant IgG monoclonal antibody control. Results are shown in the following table. The OD readings for the two antigens were significantly above the control readings (data not shown).

|  | OD Reading |
|---|---|
| Mutant antigen | 0.693 |
| Wild type antigen | 0.204 |

Binding of SMH HBs 145/G/R/II to mutant and wild type antigens was measured analogously.

Two cell lines secreting monoclonal antibody having specificity for only the variant HBsAg were deposited at the European Collection of Animal Cell Cultures (Porton Down, Salisbury, Wiltshire) on the dates and with the accession numbers shown in the following table:

| Cell line | Deposit date | Accession No. |
|---|---|---|
| SMH HBs 145/R/I | May 26, 1993 | 93052626 |
| SMH HBs 145/R/II | March 31, 1993 | 93033110 |

Binding of SMH HBs 145/R/I and SMH HBs 145/R/II to mutant and antigen was measured analogously to the method described above for SMH HBs 145/G/R/I. The same method showed that there was no significant binding to wild type antigen.

EXAMPLE 4
The Use of Monoclonal Antibody to Detect Both Mutant and Wild-type Antigen Detection of either wild type or mutant virus in serum samples with antibody secreted by SMH HBs 145/G/R/I or SMH HBs 145/G/R/II would be done using a 2 site immunoassay (Goodall et al, *Med. Lab. Sci.* 38 349–354 (1981)). The antibody could be coated onto a solid support to act as a capture phase. This would be incubated with the antigen samples for a period of time to give optimal binding. The sample would be washed from the solid support. The amount of antigen bound would be measured by incubating with labelled antibody. Antibody purified from ascitic fluid by Protein A affinity chromatography would be labelled with a radionuclide enzyme or other molecule capable of being detected eg biotin. The concentration of labelled antibody used in the assay and the time and temperature of incubation would be adjusted to give optimal binding. A blocking protein may be added at this stage to the antibody to prevent non-specific binding eg newborn calf serum or bovine serum albumin. Excess labelled antibody would be washed away and the bound label detected using the appropriate method. For example biotin-labelled antibody would be detected by an avidin-horseradish peroxidase complex. The binding of this complex being detected by ortho-phenylene diamine and hydrogen peroxide; the optical density of this colour change being measured at 492 nm. Each assay would include both positive and negative controls.

EXAMPLE 5
The Use of Monoclonal Antibody to Detect Only Mutant Antigen

Detection of only mutant virus in serum samples with antibody would be done as described in Example 4, but using antibody secreted by SMH HBs 145/R/I or SMH HBs 145/R/II instead of antibody secreted by SMH HBs 145/G/R/I or SMH HBs 145/G/R/II.

WO 94/21812 PCT/GB94/00609

16

INDICATIONS RELATING TO A DEPOSITED MICROORGANISM (PCT Rule 13bis)

| A. The indications made below relate to the microorganism referred to in the description |
|---|
| on page 7 , line 13 |

| B. IDENTIFICATION OF DEPOSIT | Further deposits are identified on an additional sheet [X] |
|---|---|
| Name of depositary institution<br>EUROPEAN COLLECTION OF ANIMAL CELL CULTURES | |
| Address of depositary institution (including postal code and country)<br>Public Health Laboratory Service<br>Centre for Applied Microbiology & Research<br>Porton Down<br>Salisbury<br>Wilts. SP4 OJG<br>GB | |
| Date of deposit<br>23 December 1992 | Accession Number<br>92122312 |

C. ADDITIONAL INDICATIONS (leave blank if not applicable) This information is continued on an additional sheet [ ]

In respect of all designated states in which such action is possible and to the extent that it is legally permissible under the law of the designated state, it is requested that a sample of the deposited micro-organism be made available only by the issue thereof to an independent expert in accordance with the relevant patent legislation, e.g. EPC Rule 28(4), U.K. Rule 17(3), Australian Regulation 3.25(3) and generally similar provisions *mutatis mutandis* for any other designated state.

D. DESIGNATED STATES FOR WHICH INDICATIONS ARE MADE (if the indications are not for all designated States)

All designated states

E. SEPARATE FURNISHING OF INDICATIONS (leave blank if not applicable)

The indications listed below will be submitted to the International Bureau later (specify the general nature of the indications e.g., 'Accession Number of Deposit')

| For receiving Office use only | For International Bureau use only |
|---|---|
| [✓] This sheet was received with the international application | [ ] This sheet was received by the International Bureau on: |
| Authorized officer | Authorized officer |

INDICATIONS RELATING TO A DEPOSITED MICROORGANISM (PCT Rule 13bis)

| A. The indications made below relate to the microorganism referred to in the description |
|---|
| on page 7, line 14 |

| B. IDENTIFICATION OF DEPOSIT | Further deposits are identified on an additional sheet [X] |
|---|---|
| Name of depositary institution | |
| EUROPEAN COLLECTION OF ANIMAL CELL CULTURES | |
| Address of depositary institution (including postal code and country) | |
| Public Health Laboratory Service<br>Centre for Applied Microbiology & Research<br>Porton Down<br>Salisbury<br>Wilts. SP4 0JG<br>GB | |
| Date of deposit | Accession Number |
| 31 March 1993 | 93033109 |

C. ADDITIONAL INDICATIONS (leave blank if not applicable)    This information is continued on an additional sheet [ ]

In respect of all designated states in which such action is possible and to the extent that it is legally permissible under the law of the designated state, it is requested that a sample of the deposited micro-organism be made available only by the issue thereof to an independent expert in accordance with the relevant patent legislation, e.g. EPC Rule 28(4), U.K. Rule 17(3), Australian Regulation 3.25(3) and generally similar provisions *mutatis mutandis* for any other designated state.

D. DESIGNATED STATES FOR WHICH INDICATIONS ARE MADE (if the indications are not for all designated States)

All designated states

E. SEPARATE FURNISHING OF INDICATIONS (leave blank if not applicable)

The indications listed below will be submitted to the International Bureau later (specify the general nature of the indications e.g., "Accession Number of Deposit")

| For receiving Office use only | For International Bureau use only |
|---|---|
| [X] This sheet was received with the international application | [ ] This sheet was received by the International Bureau on: |
| Authorized officer J.R. Lloyd-Thomas<br>R/GB 31/3/94 | Authorized officer |

WO 94/21812  PCT/GB94/00609

18

INDICATIONS RELATING TO A DEPOSITED MICROORGANISM (PCT Rule 13bis)

A. The indications made below relate to the microorganism referred to in the description
on page 7, line 15.

B. IDENTIFICATION OF DEPOSIT    Further deposits are identified on an additional sheet [X]

Name of depositary institution

EUROPEAN COLLECTION OF ANIMAL CELL CULTURES

Address of depositary institution (including postal code and country)

Public Health Laboratory Service
Centre for Applied Microbiology & Research
Porton Down
Salisbury
Wilts. SP4 0JG
GB

| Date of deposit | Accession Number |
|---|---|
| 26 May 1993 | 93052626 |

C. ADDITIONAL INDICATIONS (leave blank if not applicable)   This information is continued on an additional sheet [ ]

In respect of all designated states in which such action is possible and to the extent that it is legally permissible under the law of the designated state, it is requested that a sample of the deposited micro-organism be made available only by the issue thereof to an independent expert in accordance with the relevant patent legislation, e.g. EPC Rule 28(4), U.K. Rule 17(3), Australian Regulation 3.25(3) and generally similar provisions *mutatis mutandis* for any other designated state.

D. DESIGNATED STATES FOR WHICH INDICATIONS ARE MADE (if the indications are not for all designated States)

All designated states

E. SEPARATE FURNISHING OF INDICATIONS (leave blank if not applicable)

The indications listed below will be submitted to the International Bureau later (specify the general nature of the indications e.g., "Accession Number of Deposit")

For receiving Office use only
[✓] This sheet was received with the international application
Authorized officer J. L. Lloyd-Thomas
Ro/GB 31/03/94

For International Bureau use only
[ ] This sheet was received by the International Bureau on:
Authorized officer

INDICATIONS RELATING TO A DEPOSITED MICROORGANISM (PCT Rule 13bis)

| A. The indications made below relate to the microorganism referred to in the description |
|---|
| on page __7__, line __16__. |

| B. IDENTIFICATION OF DEPOSIT | Further deposits are identified on an additional sheet ☐ |
|---|---|
| Name of depositary institution | |
| EUROPEAN COLLECTION OF ANIMAL CELL CULTURES | |

| Address of depositary institution (including postal code and country) |
|---|
| Public Health Laboratory Service<br>Centre for Applied Microbiology & Research<br>Porton Down<br>Salisbury<br>Wilts. SP4 0JG<br>GB |

| Date of deposit | Accession Number |
|---|---|
| 31 March 1993 | 93033110 |

| C. ADDITIONAL INDICATIONS (leave blank if not applicable) This information is continued on an additional sheet ☐ |
|---|
| In respect of all designated states in which such action is possible and to the extent that it is legally permissible under the law of the designated state, it is requested that a sample of the deposited micro-organism be made available only by the issue thereof to an independent expert in accordance with the relevant patent legislation, e.g. EPC Rule 28(4), U.K. Rule 17(3), Australian Regulation 3.25(3) and generally similar provisions *mutatis mutandis* for any other designated state. |

| D. DESIGNATED STATES FOR WHICH INDICATIONS ARE MADE (if the indications are not for all designated States) |
|---|
| All designated states |

| E. SEPARATE FURNISHING OF INDICATIONS (leave blank if not applicable) |
|---|
| The indications listed below will be submitted to the International Bureau later (specify the general nature of the indications e.g., "Accession Number of Deposit") |

| For receiving Office use only | For International Bureau use only |
|---|---|
| ☑ This sheet was received with the international application | ☐ This sheet was received by the International Bureau on: |
| Authorized officer | Authorized officer |

We claim:

1. Monoclonal antibody secreted by the cell line SMH HBs 145/G/R/I (ECACC 92122312) or SMH HBs 145/G/R/II (ECACC 93033109).

2. The cell line SMH HBs 145/G/R/I (ECACC 92122312).

3. The cell line SMH HBs 145/G/R/II (ECACC 93033109).

4. A formulation comprising a monoclonal antibody according to claim 1 and a pharmaceutically acceptable carrier.

5. In a method of diagnosing Hepatitis B infection in a subject wherein the improvement comprises administering to said subject a formulation according to claim 4.

6. A method for the diagnosis of Hepatitis B, the method comprising contacting a sample suspected to contain Hepatitis B particles or antigens with a composition comprising a monoclonal antibody according to claim 1.

7. An assay kit for the detection of a Hepatitis B particle or antigen, the kit comprising a monoclonal antibody according to claim 1 and means for detecting whether the specific binding molecule is bound to a Hepatitis B particle or antigen.

8. A method for the in vivo diagnosis of Hepatitis B comprising administering to a subject a formulation according to claim 4.

* * * * *